US00PP15204P2

(12) United States Plant Patent
Kaliebe

(10) Patent No.: US PP15,204 P2
(45) Date of Patent: Oct. 5, 2004

(54) *LEUCANTHEMUM* PLANT NAMED 'LEUKAL 01'

(50) Latin Name: *Chrysanthemum leucanthemum*
Varietal Denomination: Leukal 01

(76) Inventor: Helmut Kaliebe, Kallebeweg 2, 16259 Tiefensee (DE)

( * ) Notice: Subject to any disclaimer, the term of this patent is extended or adjusted under 35 U.S.C. 154(b) by 0 days.

(21) Appl. No.: 10/616,575

(22) Filed: Jul. 10, 2003

(51) Int. Cl.[7] ..... A01H 5/00
(52) U.S. Cl. ..... Plt./285

(58) Field of Search ..... Plt./285, 284

(56) References Cited

U.S. PATENT DOCUMENTS

PP7,724 P * 11/1991 Fuess ..... Plt./296

* cited by examiner

*Primary Examiner*—Anne Marie Grunberg
*Assistant Examiner*—June Hwu
(74) *Attorney, Agent, or Firm*—Webb Ziesenheim Logsdon Orkin & Hanson, P.C.

(57) ABSTRACT

A new and distinct *Leucanthemum* plant having large inflorescences and light-yellow ray florets.

1 Drawing Sheet

Botanical classification: *Chrysanthemum leucanthemum.*
Varietal denomination: 'Leukal 01'.

BACKGROUND OF THE INVENTION

The present invention comprises a new and distinct cultivar of *Leucanthemum* plant known by the varietal name 'Leukal 01'. The new variety was discovered in 1999 in a selected breeding program in Tiefensee, Germany. The purpose of the breeding program was to discover a yellow-colored variety of *Leucanthemum.* The new variety originated as a single cultivar from a cross between 'Christine Hagemaan' (female parent, unpatented) and an unnamed, undistributed seedling (male parent, unpatented). The new variety blooms naturally in early June and has a compact growth habit with medium vigor similar to its parents, but, unlike 'Leukal 01', both parents exhibit white ray florets. Furthermore, 'Leukal 01' exhibits more distinct double flowering than both parents. The new variety begins to bloom around the same time and belongs in the same market category as 'Kiemar' (U.S. Plant Pat. No. 12,978). However, 'Leukal 01' has different colored ray florets, larger inflorescences and taller growth than 'Kiemar'. The new variety was first asexually reproduced in 1999 by vegetative tip cuttings in Tiefensee, Germany. The new variety has been trial and field tested in Germany and has been found to retain its distinctive characteristics and remain true to type through successive propagations.

The following traits distinguish 'Leukal 01' as a new and distinct cultivar:

1. The ray florets of 'Leukal 01' are light yellow.
2. 'Leukal 01' exhibits numerous ray florets.
3. 'Leukal 01' exhibits a compact plant habit.
4. The inflorescences of 'Leukal 01' are long-lasting and large.
5. 'Leukal 01' blooms in early June.

DESCRIPTION OF THE DRAWINGS

The accompanying photographic drawing illustrates a potted plant of the new variety, with the color being as nearly true as is possible with color illustrations of this type.

DESCRIPTION OF THE PLANT

Figure 1:
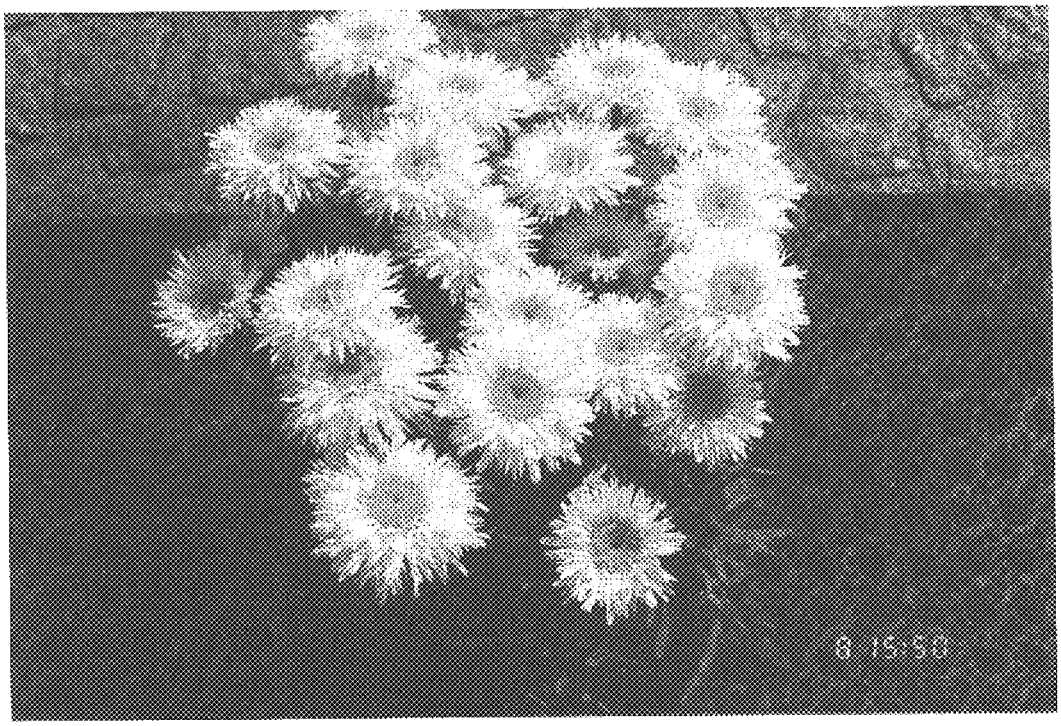

The data which defines these characteristics were collected by asexual reproductions by cuttings carried out in Tiefensee, Germany. Plants were grown at temperatures of 15–22° Celcius in 20 cm pots with regular fertilizer of 15% Nitrogen—15% Phosphate—15% Potash. The color readings were taken under approximately 4000–7000 foot candles of artificial light. Plants were 12 months old when described. Color references are primarily to the 2001 R.H.S. Colour Chart of The Royal Horticultural Society of London.

PLANT

Time to initiate roots: About 14 days at about 14° C.
Time to develop roots: About 21 days at about 14° C.
Time to produce a finished flowering plant from a rooted cutting: About 12 weeks in a 15 cm container.
Root description: Fibrous.
Height: 43.9 cm.
Plant diameter: 30.0 cm.
Vigor: Medium, compared to similar varieties.
Branching habit: Basal branching.
Lateral branches:
- *Length.*—Primary: 36 cm. Secondary: 12 cm.
- *Diameter.*—Primary: 0.5 cm. Secondary: 0.3 cm.
- *Internode length.*—1.8 cm.
- *Pubescence.*—Light.
- *Color.*—137C.

Foliage:
- *Arrangement* (*e.g., alternate, single*).—Alternate, simple.
- *Size of leaf.*—Length: 12.5 cm. Width: 2.1 cm.
- *Shape of leaf* (*generally*).—Lanceolate.
- *Shape of apex.*—Rounded to broadly acute.
- *Shape of base.*—Attenuate.
- *Aspect.*—Arcuate.
- *Margin type.*—Laciniate.
- *Pubescence.*—Upper surface: Lightly pubescent. Lower surface: Pubescent.

*Color.*—Young leaves: Upper surface: 137C. Lower surface: 144A. Mature leaves: Upper surface: 137A. Lower surface: 137B.
*Petiole.*—Shape: Oblong. Length: 0.8 cm. Diameter: 0.4 cm. Color: 137C. Surface texture: Smooth.
*Veins.*—Venation type: Pinnate. Color: Upper surface: 144A. Lower surface: 144A.

INFLORESCENCE

Bud (described before color developed):
*Shape.*—Spherical.
*Diameter.*—1.5 cm.
*Length.*—1.5 cm.
*Color.*—137D.
Natural flowering season at specified location(s): Under Northern European conditions, 'Leukal 01' flowers from early June through the end of Summer.
Appearance:
*Form.*—Actinomorphic.
Inflorescence position: Terminal.
Disc and ray floret arrangement: Acropetally on a capitulum.
Number of inflorescences per plant: 30.
Lasting quality: Thirty days.
Fragrance: None.
Disease resistance: No resistance or susceptibility observed.
Temperature tolerance: Cold tolerance to −20° C.; Heat tolerance to 35° C.
Drought tolerance: Not drought tolerant.
Size:
*Diameter.*—11.44 cm.
*Height.*—3.2 cm.
*Diameter of disc.*—4.7 cm.
Ray florets:
*Length.*—4.15 cm.
*Width.*—0.9 cm.
*Shape.*—Oblanceolate.
*Apex.*—Acute; irregular.
*Base.*—Cuneate.
*Margin.*—Entire.
*Aspect.*—Irregular, fluffy.
*Texture* (*both upper and lower surfaces*).—Smooth; glabrous.
*Number per inflorescence.*—420.
*Color.*—When opening: Upper surface: 7D. Lower surface: 7D. Fully opened: Upper surface: 4C. Lower surface: 4D.
Disc florets:
*Length.*—1.2 cm.
*Width.*—0.2 cm.
*Shape.*—Tubular.
*Number of lobes.*—Present as a single, circular structure.
*Number per inflorescence.*—450.
*Color.*—Immature: Apex: 7A. Margin: 154C. Mature: Apex: 13B. Margin: 7B.
Phyllaries:
*Length.*—4.1 cm.
*Width.*—1.5 cm.
*Shape.*—Elliptic.
*Apex.*—Acute.
*Margin.*—Entire.
*Number per inflorescence.*—70.
*Arrangement.*—Imbricate whorls.
*Texture* (*both upper and lower surfaces*).—Smooth and glabrous with light pubescence present.
*Color.*—Upper surface: 138A. Lower surface: 137B.
Peduncle:
*Length.*—5.4 cm.
*Diameter.*—0.5 cm.
*Aspect.*—Upright.
*Texture.*—Light pubescence present.
*Color.*—137B.

REPRODUCTIVE ORGANS

Androecium:
*Presence.*—On disc florets only.
*Number* (*per flower*).—1.
*Filament length.*—0.2 cm.
*Filament color.*—RHS 5A.
*Anthers.*—Shape: Oblong. Length: 0.1 cm. Color: 8A.
*Pollen.*—Color: 8A. Amount (generally): Moderate.
Gynoecium:
*Presence.*—On disc and ray florets.
*Pistils.*—Number: 1. Length: 0.8 cm. Style: Length: 0.5 cm. Color: 154C. Stigma: Shape: Bi-lobed. Color: 7B.
Seeds: None observed.

I claim:

1. A new and distinct variety of *Leucanthemum* plant substantially as shown and described.

* * * * *